United States Patent
Maschke

(10) Patent No.: US 8,795,188 B2
(45) Date of Patent: Aug. 5, 2014

(54) DEVICE AND METHOD FOR A MEDICAL INTERVENTION

(75) Inventor: Michael Maschke, Lonnerstadt (DE)

(73) Assignee: Siemens Aktiengesellschaft, Munich (DE)

( * ) Notice: Subject to any disclaimer, the term of this patent is extended or adjusted under 35 U.S.C. 154(b) by 1321 days.

(21) Appl. No.: 12/433,950

(22) Filed: May 1, 2009

(65) Prior Publication Data

US 2010/0063514 A1 Mar. 11, 2010

(30) Foreign Application Priority Data

May 9, 2008 (DE) .......................... 10 2008 022 924

(51) Int. Cl.
*A61B 19/00* (2006.01)
*A61B 17/00* (2006.01)

(52) U.S. Cl.
USPC ............ 600/534; 600/595; 600/567; 606/130

(58) Field of Classification Search
USPC ......... 5/610; 604/22, 500–522; 600/407, 411, 600/429, 424, 534, 427, 587, 595, 576, 567, 600/564, 565; 700/245; 378/42, 62, 196; 606/130, 139; 128/204.18, 911
See application file for complete search history.

(56) References Cited

U.S. PATENT DOCUMENTS

| | | | |
|---|---|---|---|
| 5,764,723 A | 6/1998 | Weinberger et al. | |
| 6,786,896 B1 | 9/2004 | Madhani et al. | |
| 7,500,784 B2 | 3/2009 | Grebner et al. | |
| 8,244,359 B2 * | 8/2012 | Gelfand et al. | 607/42 |
| 2003/0125622 A1 * | 7/2003 | Schweikard et al. | 600/437 |
| 2004/0152970 A1 * | 8/2004 | Hunter et al. | 600/424 |
| 2005/0039747 A1 * | 2/2005 | Fukunaga et al. | 128/204.18 |
| 2005/0054910 A1 * | 3/2005 | Tremblay et al. | 600/411 |
| 2005/0107808 A1 * | 5/2005 | Evans et al. | 606/139 |
| 2005/0267359 A1 | 12/2005 | Hussaini et al. | |
| 2006/0149147 A1 * | 7/2006 | Yanof | 600/424 |
| 2006/0180150 A1 | 8/2006 | Dittmann et al. | |
| 2007/0015991 A1 * | 1/2007 | Fu et al. | 600/407 |
| 2007/0183569 A1 * | 8/2007 | Boese et al. | 378/62 |

(Continued)

FOREIGN PATENT DOCUMENTS

| | | |
|---|---|---|
| DE | 10352197 A1 | 8/2005 |
| DE | 102005012700 A1 | 9/2006 |
| DE | 102005059211 A1 | 6/2007 |

OTHER PUBLICATIONS

Nagel et al.; "Needle and catheter navigation using electromagnetic tracking for computer-assisted C-arm CT interventions"; Medical Imaging 2007: Visualization and Image-Guided Procedures. Edited by Kevin R. Cleary, Michael I. Miga; Proceedings of the SPIE, vol. 6509, pp. 65090J (2007) • 1605-7422/07.

*Primary Examiner* — Ronnie Mancho

(57) ABSTRACT

The invention relates to a device and a method for a medical intervention on a patient. The device provided for carrying out the method comprises a medical instrument that is to be introduced into a moving body region of the patient, a robot which has a plurality of degrees of freedom of movement and on which the medical instrument can be disposed for guiding, and means for recording the movement of the body region, wherein the medical instrument can be introduced into the body region of the patient by means of the robot taking into account the movement of the body region and guided in the direction of a target tissue in the body of the patient.

19 Claims, 2 Drawing Sheets

(56) References Cited

U.S. PATENT DOCUMENTS

| | | | |
|---|---|---|---|
| 2008/0154389 A1* | 6/2008 | Smith et al. | 700/24 |
| 2008/0208212 A1* | 8/2008 | Camus et al. | 606/130 |
| 2008/0212737 A1* | 9/2008 | D'Souza et al. | 378/65 |
| 2008/0215181 A1* | 9/2008 | Smith et al. | 700/245 |
| 2008/0221520 A1* | 9/2008 | Nagel et al. | 604/116 |
| 2009/0149867 A1* | 6/2009 | Glozman et al. | 606/130 |

* cited by examiner

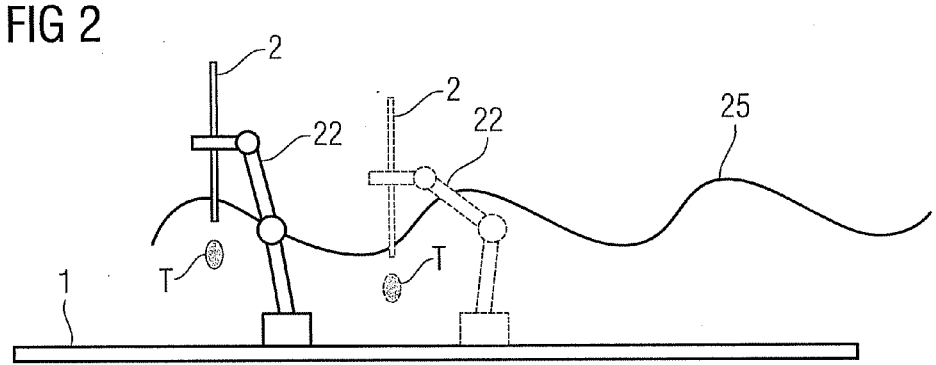
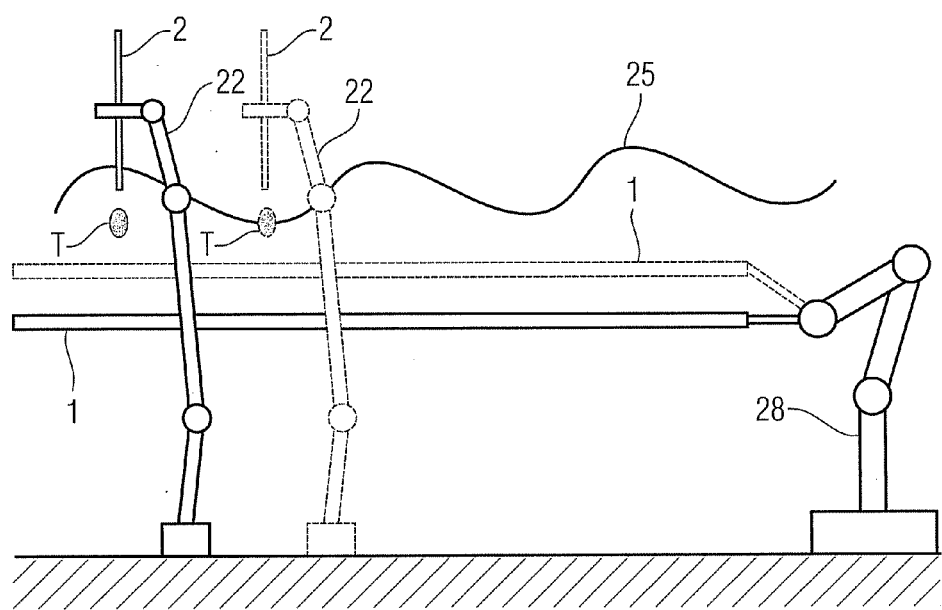

DEVICE AND METHOD FOR A MEDICAL INTERVENTION

CROSS REFERENCE TO RELATED APPLICATIONS

This application claims priority of German application No. 10 2008 022 924.5 filed May 9, 2008, which is incorporated by reference herein in its entirety.

FIELD OF THE INVENTION

The invention relates to a device and a method for a medical intervention on or in a moving region of a patient's body, wherein a medical instrument is introduced into the moving region of the patient's body and guided.

BACKGROUND OF THE INVENTION

Minimally invasive medical interventions are becoming increasingly important. Thus, in the treatment of coronary heart disease, for example, surgical bypass operations on the heart have declined considerably in favor of balloon dilatation (PTCA=Percutaneous Transluminal Coronary Angioplasty) and the use of a stent. Minimally invasive interventions are also increasing in the field of biopsies, spinal column treatments and tumor ablations.

In a minimally invasive intervention, one or more medical instruments for example are introduced into the body of a patient for treatment or diagnostic purposes. Following the introduction of a medical instrument into the patient's body, at least the tip of the medical instrument is no longer visible for a physician performing the intervention. In order to navigate the instrument in the body of the patient, the instrument must therefore be visualized in image information in a suitable way for the physician. Various systems and methods are available today for determining the position of the instrument in the patient's body during minimally invasive medical interventions, which is necessary for visualizing the instrument, in particular the tip of the instrument, in image information from inside the patient's body.

A challenge remaining in particular in the case of minimally invasive interventions, for example biopsies or tumor ablations, on or in regions of the patient's body that are moving e.g. due to the patient's respiratory movement is the precise introduction of the medical instrument into the body region and the accurate guiding of the medical instrument to a target tissue that is to be treated or examined. Thus, for example, a pulmonary tumor to be treated or examined can move by between 1 and 2 cm during a breathing cycle, which makes a minimally invasive medical intervention more difficult.

For that reason the patient is usually asked to hold his/her breath during a biopsy or tumor ablation so that a physician can introduce the treatment needle by hand into the tissue or organ region to be treated. Alternatively the physician can attempt to introduce the treatment needle into the tissue or organ region to be treated while estimating the respiratory cycle. In such cases the success of this procedure is usually dependent on the patient's cooperation and the physician's technical or surgical skill.

SUMMARY OF THE INVENTION

The object underlying the invention is therefore to disclose a device and a method of the type cited in the introduction such that a medical intervention on a patient's moving body region is made easier.

This object is achieved according to the invention by a device and a method as claimed in the claims. The device comprises a preferably rigid medical instrument which can be introduced into a moving body region of a patient, a robot which has a plurality of degrees of freedom of movement and on which the medical instrument can be disposed for guiding, and means for recording the movement of the patient's body region, wherein the medical instrument can be introduced into the patient's body region by means of the robot while taking into account the movement of the body region and guided in the direction of a target tissue in the patient's body. In this case the medical instrument is introduced automatically by the robot and guided to the target tissue, with the relative movement present per se between the body region and the medical instrument being taken into account, i.e. compensated. The body region movement to be compensated can be arbitrary movements of the patient. Preferably, however, the body region movement to be compensated will be an essentially periodic movement of the body region that is due to the cardiac or respiratory movement.

According to a variant of the invention the device has a unit, e.g. a workstation or a computer, for planning the interventions, with the starting and destination point for the guiding of the medical instrument by means of the robot having a plurality of degrees of freedom being specified based on image information from the patient's moving body region. The image information from the moving body region can be acquired preoperatively or intraoperatively by means of a computed tomography scanner, a magnetic resonance device or a C-arm x-ray device as 2D images, preferably as a 3D image. In order to obtain in particular a 3D image of the moving body region that is free of movement artifacts, the movement of the moving body region is captured already during the recording of the image information and taken into account in the reconstruction of the 3D image. The intervention can then be planned with the specification of the starting and destination point with reference to the 3D image. The automatic guiding of the medical instrument by means of the robot is accomplished, inter alia, based on this planning.

According to an embodiment variant of the invention the means for detecting the movement of the moving body region have a, for example, electromagnetic position tracking system having at least one detectable electromagnetic sensor which can be attached to the body surface, in particular to the relevant moving body region of the patient, a position tracking system having at least one camera for recording the movement of the body region and/or at least one unit for laser beam scanning of the body region. Alternatively or in addition, means for calculating the movement of the body region based on recorded anatomical images of the body region can be provided. In particular anatomical images can be acquired in particular continuously by means of x-ray radiation or ultrasound, from which images the movement of the body region can be derived. In particular when the movement of the moving body region is caused by the patient's breathing, suitable means for registering the movement of the moving body region include a respiratory belt, a respirator and/or an anesthesia ventilator, the two last-mentioned in particular when the patient is breathing by means of the respirator during the intervention or is anesthetized by means of the anesthesia ventilator. In this case the clock signal of the respirator or anesthesia ventilator that is present anyway can be used not only as a trigger signal for the preoperative or intraoperative imaging, but also for the breath-controlled guiding of the medical instrument by means of the robot. Suitable means for simultaneously detecting respiratory movements, cardiac movements and body movements are described in DE 10

2005 059 211 A1, for example. A possible respirator is disclosed e.g. in US 2006/0180150 A1.

A variant of the invention provides means for generating a movement curve of the body region based on the detected movement of the body region. The movement curve is preferably a periodic movement curve.

An embodiment variant of the invention provides that based on the movement curve the robot guiding the medical instrument is moved continuously or adjusted relative to the body region of the patient in such a way that the medical instrument moves in synchronism with the patient's body region. As a result of the continuous positioning movement or adjustment of the robot, prior to the medical intervention the medical instrument initially remains stationary relative to the relevant body region or, as the case may be, the starting point of the intervention, i.e. the continuous, periodic movement of the body region is compensated. If this is the case, the actual medical intervention can be performed with the introduction and guiding of the medical instrument by means of the robot. In this case the guiding movement of the robot is superimposed on the synchronous movement or periodic positioning movement of the robot.

According to another embodiment variant of the invention the device has an adjustable patient positioning plate on which the patient is placed, the patient positioning plate being continuously displaced or adjusted relative to the medical instrument based on the movement curve in such a way that the medical instrument and the patient's body region are essentially stationary relative to each other. In this case the continuous, periodic movement of the body region is thus compensated by a corresponding continuous, periodic countermovement of the patient positioning plate. For this purpose the patient positioning plate can be disposed on a correspondingly adjustable column, e.g. a lifting column. Preferably, however, the patient positioning plate is disposed on a robot arm of a second multi-axis robot which performs the continuous, periodic positioning movement of the patient positioning plate.

A variant of the invention provides that the device has an imaging device by means of which image information from the inside of the patient's body can be generated during the intervention in order to visualize and monitor the progress of the medical intervention. Preferably the imaging device is an x-ray device by means of which fluoroscopy images can be acquired at specific points in time with a low x-ray dose.

According to a further variant of the invention the medical instrument is a biopsy needle.

According to an embodiment variant of the invention the medical instrument is provided with at least one sensor by means of which the position of at least the distal end of the medical instrument in the body of the patient can be determined. If the sensor is, for example, an electromagnetic sensor of an electromagnetic position tracking system, following a registration of the electromagnetic position tracking system with an image of the moving body region an image of the medical instrument can be inserted into the image of the patient's moving body region. An electromagnetic position tracking system of this type, the AURORA system of the company NDI, Waterloo, Ontario, Canada, is described in "Needle and catheter navigation using electromagnetic tracking for computer-assisted C-arm CT interventions", Markus Nagel, Martin Hoheisel, Ralf Petzold, Willi A. Kalender and Ulrich H. W. Krause, Medical Imaging 2007: Visualization and Image-Guided Procedures, edited by Kevin R. Cleary, Michael I. Miga, Proc. of SPIE Volume 6509, 65090J, (2007) • 1605-7422/07/$18 • doi: 10.1117/12.709435. The electromagnetic position tracking system comprises a field generator for generating an electromagnetic field in order to determine positions and orientations of medical instruments which in each case have small induction coils in their tip. The AURORA system can determine the position and orientation of the respective instrument on the basis of the induced voltages.

According to a further variant of the invention the robot having a plurality of degrees of freedom of movement is an articulated-arm robot having at least four, preferably six degrees of freedom of movement. A robot of said kind is described in DE 10 2005 012 700 A1.

The robot can include its own stand allowing it to be disposed on a floor, on a ceiling or on a wall. The robot can, however, also be disposed on a patient positioning plate accommodating the patient. Disposing the robot having a plurality of degrees of freedom of movement on the imaging device constitutes a further alternative.

One embodiment variant of the invention provides that the robot having a plurality of degrees of freedom of movement has at least one sensor for measuring the feeding force of the medical instrument during the intervention. The sensor can be disposed in a mount or retainer of the robot for the medical instrument.

According to a variant of the invention a visual and/or an audible warning signal are/is output as a safety measure upon a first limit value for the feeding force being exceeded. A corresponding warning light and a loudspeaker can be provided for that purpose. It is signaled by means of the visual and/or audible warning signal that complications have possibly occurred during the medical intervention.

According to a further variant of the invention it is provided in a second escalation stage that after a second, higher limit value for the feeding force has been exceeded the further advancing of the medical instrument is prevented, i.e. the automatically executing medical intervention is stopped.

BRIEF DESCRIPTION OF THE DRAWINGS

An exemplary embodiment of the invention is illustrated in the attached schematic drawings, in which:

FIG. 2 shows the positioning movement of a robot guiding a medical instrument that is synchronized with a patient's breathing, and FIG. 3 shows the positioning movement of a patient positioning plate guided by a robot that is synchronized with a patient's breathing.

DETAILED DESCRIPTION OF THE INVENTION

Figure 1:
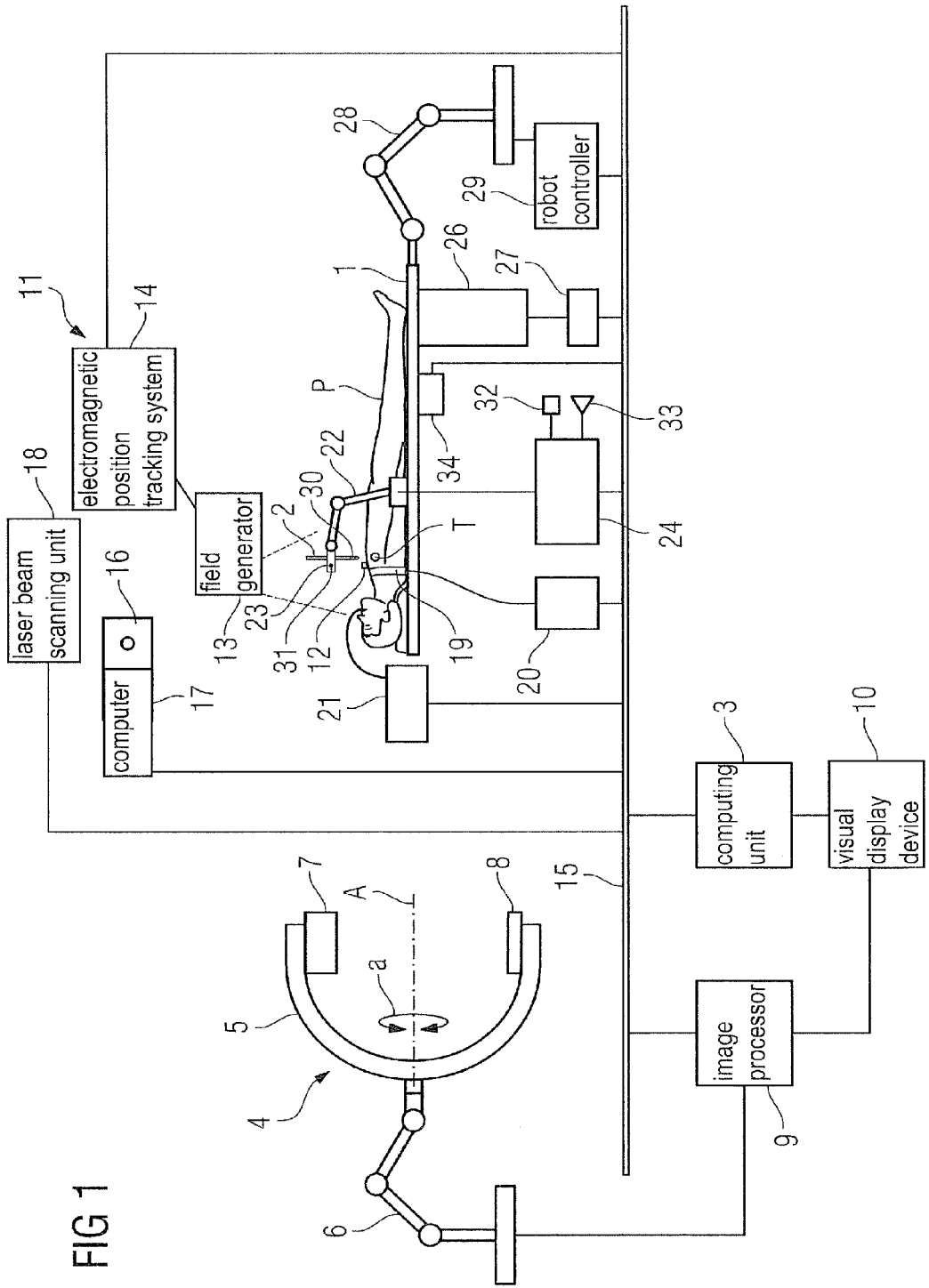
FIG. 1 shows a device for performing a medical intervention on a patient.

FIG. 1 shows a device for performing a medical intervention on a patient P placed on a schematically depicted patient positioning plate 1. In the case of the present exemplary embodiment the intervention is a biopsy in the thoracic region of the patient P, wherein a medical instrument in the form of a biopsy needle 2 is introduced into the thoracic region of the patient P in order to remove a tissue sample from a target tissue in the form of a tumor T.

Performing the biopsy in the thoracic region proves difficult to the extent that the thoracic region containing the tumor T moves as a result of the patient's breathing, with the tumor T therefore representing a moving target on which the aim is to score a direct hit by means of the biopsy needle.

In order to be able to perform the biopsy successfully, the latter is first prepared using a computing unit 3 for the purpose of planning the intervention. In the course of the preparation for the intervention image information is initially acquired from the thoracic region of the patient P, in the present case by means of a C-arm x-ray apparatus 4. The C-arm 5 of the C-arm x-ray apparatus 4 is disposed on a multi-axis robot 6 and supports an x-ray source 7 and an x-ray receiver 8 which are located opposite each other. The C-arm 5 is adjustable in a per se known manner about its angulation axis A in the directions of the double arrow a. The C-arm 5 is also adjustable by means of the robot 6 in such a way that the C-arm 5 can be arranged relative to the patient P such that by rotating the C-arm 5 about the angulation axis A a series of 2D projections of the thoracic region of the patient P can be recorded from different projection directions without the presence of the biopsy needle 2.

In parallel with the recording of the 2D projections, the movement of the thoracic region of the patient P is also recorded. Various devices are suitable for this purpose. A first possibility consists in the use of an electromagnetic position tracking system 11, whereby an electromagnetic sensor 12 of the position tracking system 11 is disposed in the thoracic region of the patient P. A field generator 13 of the position tracking system 11 generates an electromagnetic field in which the sensor 12 is located in order to be able to determine the positions of the sensor 12 provided with small induction coils. On the basis of the voltages induced in the coils of the sensor 12 a computing device 14 of the position tracking system 11, which device is connected to the sensor 12 in a manner that is not shown, can determine the positions of the sensor 12 and thereby continuously calculate a movement curve or, in the case of the present exemplary embodiment, a respiratory curve of the thoracic region of the patient P over time.

Since the computing device 14 of the position tracking system 11 is connected to a common data bus 15, the movement curve is also available to an image processor 9 of the C-arm x-ray apparatus 4. A specific movement phase of the thoracic region, for example the patient's maximum inhalation phase, can be selected with the aid of the movement curve. The image processor then uses only the 2D projections that were recorded essentially at that time for the reconstruction of a volume data set of the thoracic region of the patient P. In this way a movement-artifact-free volume data set of the thoracic region of the patient P is obtained, from which in turn a 3D image of the thoracic region can be generated and displayed on a visual display device 10.

Alternatively or in addition, the movement curve can also be determined with the aid of an optical position tracking system having at least one camera 16. In this case a computer 17 evaluates the preferably continuously recorded camera images of the thoracic region of the patient P and calculates the movement curve of the thoracic region. A further possibility of determining the movement curve consists in the use of a unit 18 for continuous laser beam scanning of the thoracic region of the patient P. A respiratory belt 19 with evaluation unit 20 can also be used for determining the movement curve. If the patient P is assisted in his/her breathing by means of a respirator 21 during the biopsy or, as the case may be, is anesthetized by means of an anesthesia ventilator, the movement curve of the thoracic region can also be derived directly based on the gating signal for the respiratory gating of the respirator 21 or, as the case may be, based on the gating signal of the anesthesia ventilator 21. According to a further variant, x-ray images of the thoracic region of the patient P can be acquired continuously by means of the C-arm x-ray apparatus 4, which images the image processor 9 evaluates with regard to the movement of the thoracic region. Based on the evaluation the image processor can determine or calculate a movement curve of the thoracic region.

In the following it is assumed that the electromagnetic position tracking system 11 is used for the continuous determination of the movement curve of the thoracic region of the patient P.

In the foregoing it is described that the 2D projections used for the movement-artifact-free reconstruction are selected retrospectively. Since all the aforementioned means for determining the movement curve of the thoracic region are connected to the data bus 15, the C-arm x-ray apparatus 4 can, however, also be operated during the acquisition of the 2D projections in such a way that a 2D projection is recorded only when the thoracic region is located in a specific movement phase. In this case the C-arm x-ray apparatus 4 is therefore triggered accordingly during the recording of the 2D projections based on the movement curve. The 2D projections thus acquired are then used for the movement-artifact-free reconstruction of a volume data set or, as the case may be, a 3D image.

When a 3D image of the thoracic region of the patient P has been generated, this can be used as a basis for planning the intervention, whereby the starting point and destination point for the guiding of the biopsy needle 2 are specified, inter alia. In this case the movement curve can be displayed continuously on the visual display device 10 connected to the computing unit 3 for planning purposes.

According to the invention, however, the biopsy needle 2 is guided during the medical intervention not by hand, but by a robot having a plurality of degrees of freedom of movement, by an articulated-arm robot 22 in the case of the present exemplary embodiment. For that purpose the biopsy needle 2 is disposed in a retainer 23 of the articulated-arm robot 22. In the present case the articulated-arm robot 22 is disposed on the patient positioning plate 1 and connected by means of its robot controller 24 to the data bus 15.

The articulated-arm robot 22 provided in a defined manner with the biopsy needle 2 is registered in a per se known manner, for example landmark-based, with the 3D image of the thoracic region, by which is understood, inter alia, the determining of a coordinate transformation between a coordinate system associated with the 3D image and one associated with the articulated-arm robot 22. Thereafter the articulated-arm robot 22 can guide the biopsy needle 2 from the starting point to the destination point in the thoracic region of the patient P, as specified during the planning phase.

Since the thoracic region moves, the introduction of the biopsy needle 2 and the guiding of the biopsy needle 2 are also performed taking into account the movement of the thoracic region.

According to a first embodiment variant of the invention the articulated-arm robot 22 guides the biopsy needle 2 based on the movement curve continuously determined by means of the position tracking system 11 and available to the robot controller 24 via the data bus 15. In this case the articulated-arm robot 22 and the position tracking system 11 are likewise registered with each other. In the case of the present exemplary embodiment of the invention the registration is performed by means of an electromagnetic sensor 30 of the electromagnetic position tracking system 11, which sensor is disposed in a defined manner in or on the biopsy needle 2, which itself is accommodated in a defined manner in the retainer 23 of the articulated-arm robot 22. In this way it is possible, as shown schematically in FIG. 2, for the articulated-arm robot 22 to be moved or adjusted based on the movement curve 25 relative to the thoracic region or, as the case may be, to the tumor T of the patient P by displacements about its axes in such a way that the biopsy needle 2 moves in synchronism with the thoracic region or, as the case may be, the tumor T of the patient P (only the tumor T is shown in FIG. 2). By this means the movement of the thoracic region or, as the case may be, of the tumor T in relation to the biopsy needle 2 is compensated and the biopsy needle 2 can be introduced into the thoracic region by means of a guiding movement of the articulated-arm robot 22 superimposed on the compensation movement of the articulated-arm robot 22 and guided to the tumor T.

According to an alternative embodiment variant of the invention it is not the articulated-arm robot 22 which performs the compensation movement, but the patient positioning plate 1 which is disposed on an adjustable column 26 with associated controller 27. In this case, however, the articulated-arm robot 22 is disposed, not on the patient positioning plate 1, but (in a manner not shown explicitly) on the floor, on the ceiling or on a wall of a room and is stationary except for the guiding movement. Based on the movement curve continuously determined by means of the position tracking system 11, the controller 27 adjusts the patient positioning plate 1 carrying the patient P relative to the biopsy needle 2 in such a way that the biopsy needle 2 and the thoracic region of the patient P or, as the case may be, the tumor T are essentially stationary relative to each other. For that purpose the patient positioning plate 1 performs a movement counter to the movement of the thoracic region or, as the case may be, the tumor T. In this case the position tracking system 11 and the patient positioning plate 1 adjustable by means of the controller 27 are registered with each other, for which purpose for example (in a manner not shown) one or more sensors of the position tracking system 11 can be disposed in a defined manner on the patient positioning plate 1. While other body regions of the patient, for example the feet, are in movement in this case, the movement of the thoracic region or, as the case may be, of the tumor T relative to the biopsy needle 2 is compensated. Accordingly, the biopsy needle 2 can be introduced precisely into the thoracic region by means of the articulated-arm robot 22 and guided with pinpoint accuracy to the tumor T.

Alternatively, instead of being disposed on the column 26 the patient positioning plate 1 can also be disposed on a multi-axis robot 28 with robot controller 29 and be moved accordingly by the latter. In this case the robot 28 adjusts the patient positioning plate 1 based on the movement curve 25, as illustrated in FIG. 3.

In the case of the present exemplary embodiment of the invention the biopsy needle 2 is, as already mentioned, provided in the region of its tip with an electromagnetic sensor 30 of the electromagnetic position tracking system 11, such that the position in particular of the tip of the biopsy needle can be determined and following a registration of the position tracking system 11 with the 3D image of the thoracic region of the patient P already used for the planning of the intervention can be inserted into the 3D image. In this way the progress of the biopsy can be tracked, and in particular the respective current position of the biopsy needle 2 relative to the tumor T visualized.

Furthermore, 2D x-ray projections or fluoroscopic images of the thoracic region of the patient P can be recorded with a minimally low x-ray dose by means of the C-arm x-ray apparatus 4 at specific points in time during the biopsy in order to track the progress of the biopsy. It is also possible in this case to overlay the currently recorded 2D x-ray projections or fluoroscopic images onto the 3D image of the patient's thoracic region.

In the case of the present exemplary embodiment of the invention the articulated-arm robot 22, in particular the retainer 23 of the articulated-arm robot 22, also has a sensor 31 for measuring the feeding force of the biopsy needle 22. The sensor 31 can be a piezoelectric sensor, for example. In this way the feeding force can be monitored during the biopsy and if an increased feeding force occurs, which is indicative of a problem, for example a bone located in the biopsy path, an intervention can be made to protect the patient P during the biopsy.

In the case of the present exemplary embodiment, the sensor signals of the sensor 31 are evaluated by the robot controller 24. If the measured feeding force exceeds a first predefinable limit value, which can be based on empirical values, a visual and an audible warning signal are output which signal a problem to the physician monitoring the automatic execution of the biopsy. Toward that end, a warning lamp 32 and a loudspeaker 33 are connected to the robot controller and are controlled by the robot controller 24. If the feeding force continues to increase during the biopsy and the physician does not react accordingly, after a second predefinable limit value, which can likewise be based on empirical values, has been exceeded the further automated advancing of the biopsy needle 2 by means of the articulated-arm robot 22 is stopped. Otherwise the biopsy is continued until the removal of the tissue sample from the tumor T.

In contrast to the above-described exemplary embodiments, the articulated-arm robot 22 can also be disposed on the C-arm x-ray apparatus 4 if the latter is located next to the patient positioning plate 1 or, as the case may be, next to the patient P during the biopsy.

For the rest, the C-arm 5 and also the patient positioning plate 1 do not necessarily have to be disposed on a robot.

Furthermore, a control unit 34 disposed close to the patient can be provided on the patient positioning plate 1 for the C-arm x-ray apparatus 4, the articulated-arm robot 22, the column 26, the robot 28 and/or the position tracking system 11.

The medical instrument does not necessarily have to be a biopsy needle 2. Rather, other, in particular rigid, medical instruments can also be guided by means of the articulated-arm robot.

The invention claimed is:

1. A device for a medical intervention, comprising
a robot having a plurality of degrees of freedom of movement;
a recording device that records a movement of a moving body region of a patient; and
a medical instrument disposed on the robot that is to be introduced into the moving body region by the robot taking into account the movement of the body region, such that the moving body region is essentially stationary relative to the medical instrument as the medical instrument is guided in a direction of a target tissue in the moving body region,
wherein the robot comprises a sensor that measures a feeding force of the medical instrument during the intervention.

2. The device as claimed in claim 1, further comprising a unit for planning the intervention.

3. The device as claimed in claim 1, wherein the robot guides the medical instrument based on image information of the moving body region.

4. The device as claimed in claim 1, wherein the recording device comprises:

a position tracking system comprising:
- a detectable sensor that is attached to a body surface of the patient, and
- a camera that records the movement of the moving body region;

a scanning unit that scans the body region with a laser beam;

a processor that calculates the movement of the moving body region based on an anatomical image of the moving body region;

a respiratory belt;

a respirator; and an anesthesia ventilator.

5. The device as claimed in claim 1, wherein further comprising a device that generates a movement curve of the moving body region based on the movement of the moving body region.

6. The device as claimed in claim 5, wherein the robot moves relative to the moving body region and guides the medical instrument based on the movement curve and the medical instrument moves synchronously with the moving body region.

7. The device as claimed in claim 5, further comprising an adjustable patient positioning plate on which the patient is placed, wherein the patient positioning plate is adjusted relative to the medical instrument based on the movement curve so that the medical instrument and the moving body region are stationary relative to each other.

8. The device as claimed in claim 7, wherein the patient positioning plate is disposed on a robot arm of a second robot.

9. The device as claimed in claim 7, wherein the robot is arranged on the patient positioning plate.

10. The device as claimed in claim 1, further comprising an imaging device that generates an image information of an inside of the moving body region during the intervention.

11. The device as claimed in claim 10, wherein the imaging device is an x-ray device.

12. The device as claimed in claim 10, wherein the robot is arranged on the imaging device.

13. The device as claimed in claim 1, wherein the medical instrument is a biopsy needle.

14. The device as claimed in claim 1,
wherein the medical instrument comprises a sensor that determines a position of a distal end of the medical instrument in the moving body region, and
wherein the sensor is an electromagnetic sensor.

15. The device as claimed in claim 1, wherein the robot is an articulated-arm robot having at least four degrees of freedom of movement.

16. The device as claimed in claim 1, wherein the robot comprises a separate stand that disposes the robot on a floor, on a ceiling, or on a wall.

17. The device as claimed in claim 1, wherein a visual or an audible warning signal is output when the feeding force exceeds a first limit value.

18. The device as claimed in claim 17, wherein the medical instrument is prevented from further advancing when the feeding force exceeds a second limit value.

19. A method for performing a medical intervention, comprising:
- providing a robot having a plurality of degrees of freedom of movement;
- disposing a medical instrument on the robot;
- recording a movement of a moving body region of a patient;
- introducing the medical instrument into the moving body region by the robot taking into account the movement of the moving body region; and
- guiding the medical instrument in the moving body region by the robot in a direction of a target tissue,
- wherein the robot comprises a sensor that measures a feeding force of the medical instrument during the intervention.

* * * * *